(12) United States Patent
Bureau

(10) Patent No.: US 10,080,843 B2
(45) Date of Patent: Sep. 25, 2018

(54) METHOD OF MANUFACTURE FOR A MINIATURIZED DRUG DELIVERY DEVICE

(71) Applicant: Becton Dickinson France, Le Pont de Claix (FR)

(72) Inventor: Christophe Bureau, Saint-Martin d'Uriage (FR)

(73) Assignee: Becton Dickinson France, Le Pont-de-Claix (FR)

( * ) Notice: Subject to any disclaimer, the term of this patent is extended or adjusted under 35 U.S.C. 154(b) by 379 days.

(21) Appl. No.: 15/147,367

(22) Filed: May 5, 2016

(65) Prior Publication Data
US 2016/0243307 A1   Aug. 25, 2016

Related U.S. Application Data

(62) Division of application No. 14/384,269, filed as application No. PCT/IB2013/000875 on Mar. 13, 2013, now Pat. No. 10,010,676.
(Continued)

(51) Int. Cl.
*A61M 5/31* (2006.01)
*A61M 37/00* (2006.01)
(Continued)

(52) U.S. Cl.
CPC .......... *A61M 5/3129* (2013.01); *A61M 5/145* (2013.01); *A61M 5/155* (2013.01);
(Continued)

(58) Field of Classification Search
CPC ............ A61M 5/3129; A61M 37/0015; A61M 5/155; A61M 5/145; A61M 5/5086;
(Continued)

(56) References Cited

U.S. PATENT DOCUMENTS 5,900,238 A   5/1999   Gombotz et al.
5,942,242 A   8/1999   Mizushima et al.
(Continued)

FOREIGN PATENT DOCUMENTS

JP   2005525141 A   8/2005
JP   2006500086 A   1/2006
(Continued)

OTHER PUBLICATIONS

Song et al., Microneedle Delivery of H5N1 Influenza Virus-Like Particles to the Skin Induces Long-Lasting B- and T-Cell Responses in Mice, Clinical and Vaccine Immunology, Sep. 2010, pp. 1381-1389, vol. 17, No. 9.

*Primary Examiner* — David Walczak
(74) *Attorney, Agent, or Firm* — The Webb Law Firm

(57) ABSTRACT

A method of making a delivery device for therapeutic agent, drug or vaccine. The method includes providing a flat panel wafer, forming a plurality of reservoirs, with each reservoir defining a cavity, within the flat panel wafer, and attaching a cover layer across the plurality of reservoirs. The method also includes filling the plurality of reservoirs with at least one of a therapeutic agent, drug, and vaccine to form a plurality of filled reservoirs, and providing a housing portion adjacent each of the plurality of filled reservoirs to form a composed layer. The method also includes separating the composed layer into a plurality of delivery devices, wherein each delivery device includes a reservoir. The delivery device may be suitable for self-injection use.

14 Claims, 8 Drawing Sheets

Related U.S. Application Data

(60) Provisional application No. 61/669,846, filed on Jul. 10, 2012, provisional application No. 61/661,032, filed on Jun. 18, 2012, provisional application No. 61/661,020, filed on Jun. 18, 2012, provisional application No. 61/610,189, filed on Mar. 13, 2012, provisional application No. 61/610,184, filed on Mar. 13, 2012.

(51) Int. Cl.
| | | |
|---|---|---|
| *A61M 5/155* | (2006.01) | |
| *B65B 3/10* | (2006.01) | |
| *A61M 5/50* | (2006.01) | |
| *A61M 5/24* | (2006.01) | |
| *A61M 5/145* | (2006.01) | |
| *A61M 5/142* | (2006.01) | |

(52) U.S. Cl.
CPC ...... *A61M 5/5086* (2013.01); *A61M 37/0015* (2013.01); *B65B 3/10* (2013.01); *A61M 5/14244* (2013.01); *A61M 5/2425* (2013.01); *A61M 2005/14513* (2013.01); *A61M 2005/314* (2013.01); *A61M 2037/0023* (2013.01); *A61M 2037/0053* (2013.01); *A61M 2205/33* (2013.01); *A61M 2205/59* (2013.01)

(58) Field of Classification Search
CPC .. A61M 2037/0023; A61M 2037/0053; A61M 5/2425; A61M 5/14244; A61M 2005/314; A61M 2005/14513; A61M 2205/33; A61M 2205/59; A61M 2005/14252; A61M 2005/14288; B65B 3/10; B65B 3/14; B65B 3/18
See application file for complete search history.

(56) References Cited

U.S. PATENT DOCUMENTS

| | | | |
|---|---|---|---|
| 6,045,534 | A | 4/2000 | Jacobsen et al. |
| 6,086,562 | A | 7/2000 | Jacobsen et al. |
| 6,099,853 | A | 8/2000 | Hertelendy et al. |
| 6,494,865 | B1 | 12/2002 | Alchas |
| 6,565,532 | B1 | 5/2003 | Yuzhakov et al. |
| 6,569,143 | B2 | 5/2003 | Alchas et al. |
| 6,896,666 | B2 | 5/2005 | Kochamba |
| 6,929,950 | B2 | 8/2005 | Canham et al. |
| 6,953,455 | B2 | 10/2005 | Cho et al. |
| 6,958,691 | B1 | 10/2005 | Anderson et al. |
| 6,991,779 | B2 | 1/2006 | Steiner et al. |
| 7,135,191 | B2 | 11/2006 | Hertelendy et al. |
| 7,225,807 | B2 | 6/2007 | Papania et al. |
| 7,429,258 | B2 | 9/2008 | Angel et al. |
| 7,670,314 | B2 | 3/2010 | Wall et al. |
| 7,758,855 | B2 | 7/2010 | Kopecko et al. |
| 7,867,405 | B2 | 1/2011 | Spitz et al. |
| 7,896,841 | B2 | 3/2011 | Wall et al. |
| 7,998,119 | B2 | 8/2011 | Yeshurun et al. |
| 8,007,466 | B2 | 8/2011 | Yeshurun et al. |
| 9,844,631 | B2 * | 12/2017 | Bureau ............... A61M 5/3129 |
| 2002/0009463 | A1 | 1/2002 | Raa et al. |
| 2003/0045492 | A1 | 3/2003 | Tang et al. |
| 2003/0104010 | A1 | 6/2003 | Raa et al. |
| 2003/0153900 | A1 | 8/2003 | Aceti et al. |
| 2003/0190332 | A1 | 10/2003 | Gilad et al. |
| 2004/0092875 | A1 | 5/2004 | Kochamba |
| 2004/0134495 | A1 | 7/2004 | Eigemann et al. |
| 2005/0165380 | A1 | 7/2005 | Kochamba |
| 2005/0209566 | A1 | 9/2005 | Yeshurun et al. |
| 2006/0015061 | A1 | 1/2006 | Kuo et al. |
| 2006/0239931 | A1 | 10/2006 | Eyles et al. |
| 2006/0264926 | A1 | 11/2006 | Kochamba |
| 2007/0010810 | A1 | 1/2007 | Kochamba |
| 2007/0060837 | A1 | 3/2007 | Cho et al. |
| 2007/0088248 | A1 | 4/2007 | Glenn et al. |
| 2007/0276320 | A1 | 11/2007 | Wall et al. |
| 2007/0293826 | A1 | 12/2007 | Wall et al. |
| 2008/0131377 | A1 | 6/2008 | Eyles et al. |
| 2009/0012494 | A1 | 1/2009 | Yeshurun et al. |
| 2009/0054842 | A1 | 2/2009 | Yeshurun et al. |
| 2009/0069788 | A1 | 3/2009 | Yeshurun et al. |
| 2009/0182306 | A1 | 7/2009 | Lee et al. |
| 2010/0111984 | A1 | 5/2010 | D'Souza |
| 2010/0185177 | A1 | 7/2010 | Gillum |
| 2010/0211005 | A1 | 8/2010 | Edwards et al. |
| 2011/0040245 | A1 | 2/2011 | Garcia De Castro Andrews |
| 2011/0059150 | A1 | 3/2011 | Kendall et al. |
| 2011/0238038 | A1 | 9/2011 | Sefi et al. |
| 2011/0282298 | A1 | 11/2011 | Agian et al. |

FOREIGN PATENT DOCUMENTS

| | | |
|---|---|---|
| JP | 2009513365 | 4/2009 |
| WO | 02083213 A1 | 10/2002 |
| WO | 2006031856 A2 | 3/2006 |
| WO | 2009023549 A2 | 2/2009 |
| WO | 2010007565 A2 | 1/2010 |
| WO | 2010067319 A2 | 6/2010 |
| WO | 2011042542 A1 | 4/2011 |

* cited by examiner

METHOD OF MANUFACTURE FOR A MINIATURIZED DRUG DELIVERY DEVICE

CROSS-REFERENCE TO RELATED APPLICATIONS

The present application is a divisional application of U.S. patent application Ser. No. 14/384,269 filed Sep. 10, 2014, now U.S. Pat. No. 10,010,676, which is the United States national phase of International Application No. PCT/IB2013/000875 filed Mar. 13, 2013, which claims priority to U.S. Provisional Application No. 61/610,184 filed Mar. 13, 2012; 61/610,189 filed Mar. 13, 2012; 61/661,032 filed Jun. 18, 2012; 61/661,020 filed Jun. 18, 2012; and 61/669,846 filed Jul. 10, 2012.

BACKGROUND OF THE INVENTION

Field of the Invention

The invented method relates generally to the manufacture of an injection device, and, more specifically, to a method of manufacturing a miniaturized device for injection of a therapeutic agent, such as a vaccine by an individual without medical training.

Description of Related Art

Current vaccination programs have numerous financial and logistical problems. In emerging countries, public health officials have, so far, been largely unsuccessful in carrying out large-scale vaccination initiatives. One reason for the lack of success stems from the logistical difficulties in transporting large populations to a limited number of distant immunization clinics where professionals have sufficient expertise to perform the inoculation. While charitable organizations and non-governmental organizations provide considerable amounts of money to cover vaccine costs, the lack of infrastructure has prevented these vaccines from reaching many rural populations.

In developed countries, doctor shortages are increasing and long standing policy issues have made the distribution of vaccines complex. In times of increased need for vaccines, vaccine distribution is often managed "on-the-fly". As the average population in these developed countries continues to increase, the need for vaccinations in response to flu outbreak will certainly increase. Further, the existing immunization infrastructures are insufficient for responding to pandemic situations. World health experts continue to caution that as global integration increases, the possibility of a rapidly spreading world-wide flu pandemic continues to increase.

The problems associated with providing immunization on a large scale generally result from a combination of: (1) how vaccinations are administered; and (2) currently available injection devices. Receiving a vaccine or drug through injection most typically requires at least one appointment with a medical provider such as a General Practitioner (GP). The injection is generally performed by a trained professional such as a nurse. In many countries, the cost of a GP appointment, not including the cost of the drug or injection itself, is significant. Further, many countries are currently experiencing a shortage of GPs and other trained medical professionals. This shortage could be alleviated in part if medical professionals spent less time performing trivial procedures, such as injections, and more time diagnosing and treating more complex medical conditions. It is evident that significant savings in time and expense could be realized if untrained individuals could perform injections of vaccines and other therapeutic agents on themselves.

A wide variety of hypodermic injection devices for fluid injections are commercially available. Most hypodermic injections are intended to be intramuscular, requiring that a hypodermic needle penetrates through an individual's skin layer and subcutaneous tissue and into the muscle. Needles of this type generally cause pain, damage to the skin at the site of insertion, and bleeding, which increases the risk of disease transmission and infection at the wound site. Intramuscular injections also generally require administration by one trained in needle use. Problems of pain, wound formation, and the general skill required to perform the injection mean that intramuscular injections are difficult to perform outside of a medical facility and especially difficult for untrained individuals to perform self-injections.

An alternative delivery technique is the transdermal patch, which relies on diffusion of a drug across the skin. However, transdermal delivery devices are not useful for many drugs, due to the poor permeability (i.e., effective barrier properties) of the skin. The rate of diffusion depends in part on the size and hydrophilicity of the drug molecules and the concentration gradient across skin layers. In fact, few drugs have the necessary properties to be effectively delivered through the skin by passive diffusion. While providing varying degrees of enhancement can increase permeability for some substances, these techniques are not suitable for all types of drugs. In some cases, transdermal drug delivery is also painful and inconvenient for users.

A second alternative drug delivery possibility is a mini-needle syringe. Mini-needle syringes allow for intradermal injection of a drug at clinically relevant rates through one or more layers of skin with minimal damage, pain, or irritation to the surrounding tissue. Mini-needle syringes include a needle shaft having a cross-sectional dimension of between about 1 μm and 500 μm. In many cases, the puncture site formed by a mini-needle is less than about 0.2 μm in diameter. The small diameter of the puncture site reduces pain and increases healing time, significantly reducing the possibility of infection. An example of such an intradermal delivery device and needle assembly is disclosed in U.S. Pat. No. 6,494,865 assigned to Becton, Dickinson and Company and incorporated herein by reference. However, it is recognized that while mini-needle syringes effectively reduce pain, many individuals are, nevertheless, intimidated by the prospect of performing an injection on themselves. Specifically, research indicates that individuals without medical training are still intimidated by the prospect of performing an injection on themselves. Thus, it can be concluded that it is the fear and anticipation of the injection process, rather than the pain itself, that prevents many individuals from performing injections on themselves.

More recently still, miniaturized drug delivery devices based on patch-like designs have been envisioned which further miniaturize the needle assembly. These devices are manufactured using micro-scale manufacturing techniques developed for the semiconductor industry and are suitable for mass production. Typically, such devices involve microneedles produced from a substrate such as a silicon base by, for example, press extrusion techniques in which force exerted on a top portion of the substrate produces a pointed tip extending from the base of the substrate. Often the tip portions of the microneedles are shaped and dimensioned to carry a biologically active substance. The plurality of needles pierces and penetrates into target cells within tissue, so that the biological substance is transferred from the tip portion and deposited within the target cells.

However, such tip loading is not effective to deliver a precisely metered dose of a biologically active substance.

Generally, medical treatment methodologies that include injection into a patient require precisely controlling the amount of drug delivered which cannot be accomplished with tip coating. Further, microneedles produced by this process pierce the stratum corteum of the skin, but do not extend into the dermis. Accordingly, such microneedles are generally unable to facilitate delivery of drugs which cannot diffuse through the dermis layer of skin. Vaccines are an example of a therapeutic agent that cannot diffuse through the epidermis or stratum corteum.

Therefore, it would be desirable to provide an injection device and method of manufacture thereof for intradermal delivery of a therapeutic or preventative agent configured for self-injection.

SUMMARY OF THE INVENTION

Provided herein is a method of manufacture for a miniaturized device for self-injection of a therapeutic agent.

In accordance with an embodiment of the present invention, a method of making a delivery device for a therapeutic agent, drug, or vaccine includes providing a flat panel wafer. The method also includes forming a plurality of reservoirs, with each reservoir defining a cavity, within the flat panel wafer, and attaching a cover layer across the plurality of reservoirs. The method also includes filling the plurality of reservoirs with at least one of a therapeutic agent, drug, and vaccine to form a plurality of filled reservoirs. The method further includes providing a housing portion adjacent each of the plurality of filled reservoirs to form a composed layer, and separating the composed layer into a plurality of delivery devices, wherein each delivery device includes a reservoir.

In certain embodiments, the flat panel wafer is at least one of glass and silicon. The forming of a plurality of reservoirs within the flat panel wafer may be achieved by thermal slumping. The flat panel wafer may have a thickness of about 400 μm and may be substantially impermeable to water and oxygen. The flat panel wafer may be formed of a material that is substantially inert or coated with a material that is substantially inert and may be formed by at least one of float processing and fusion processing.

Optionally, the flat panel wafer may have initial dimensions of from about 14 to about 17 square inches, and from about 40 to about 50 delivery devices may be produced from the single flat panel wafer. Each of the reservoirs may be dimensioned to receive from about 100 μl to about 0.5 mL of a therapeutic agent, drug, or vaccine therein. In certain embodiments, the method may include forming an access hole within each reservoir of the plurality of reservoirs. The plurality of access holes may be simultaneously formed within a plurality of reservoirs and each access hole may be dimensioned to receive a 30 gauge needle therein.

The cover layer may be bonded or thermally annealed to the flat panel wafer such that each of the cavities of the plurality of reservoirs are accessible only through the access holes. The plurality of reservoirs may be simultaneously filled with at least one of a therapeutic agent, drug, or vaccine. The method may also include sealing the filled reservoirs with a thin polymer layer and providing a plurality of needles adjacent the housing such that each of the plurality of needles is aligned with a reservoir of the plurality of reservoirs. The housing may include a bottom support layer.

In a further embodiment of the method, the step of filling the plurality of reservoirs includes introducing a filling cannula to the reservoir, removing air contained in the reservoir from the reservoir, through the filling cannula, to create a vacuum in the reservoir, and passively drawing the therapeutic agent, drug, or vaccine into the reservoir through the filling cannula, as a result of a pressure difference between the vacuum in the reservoir and the therapeutic agent, drug, or vaccine. The step of filling the reservoir may also further include removing the filling cannula from the reservoir and covering an opening formed by the filling cannula with an adhesive film to seal the reservoir. Optionally, a plurality of the filling cannulae are disposed on a counter-wafer. The counter-wafer may be configured such that each filling cannula is simultaneously introduced to a reservoir for simultaneously filling a plurality of reservoirs. A device produced by this methodology is also intended herein.

In accordance with yet another embodiment of the present invention, a method of making a delivery device for therapeutic agent, drug, or vaccine includes providing a flat panel wafer, and forming a plurality of reservoirs, with each reservoir defining a cavity, within the flat panel wafer is provided. The method also includes filling the plurality of reservoirs with at least one of a therapeutic agent, drug, and vaccine to form a plurality of filled reservoirs, and providing a bottom support layer adjacent the plurality of reservoirs to form a composed layer. The method further includes providing a plurality of needles, each needle engageable with a single filled reservoir of the plurality of reservoirs, and separating the composed layer into a plurality of delivery devices, wherein each delivery device comprises a reservoir.

In certain embodiments, the forming of the plurality of reservoirs within the flat panel wafer is achieved by thermal slumping. The flat panel wafer may have a thickness of about 400 μm. The flat panel wafer may be substantially impermeable to water and oxygen, and may be formed of a material that is substantially inert or coated with a material that is substantially inert. The flat panel wafer may be formed by at least one of float processing and fusion processing.

Optionally, the flat panel wafer may have an initial dimension of from about 14 to about 17 square inches, wherein from about 40 to about 50 delivery devices may be produced from the single flat panel wafer. Each of the reservoirs may be dimensioned to receive from about 100 μl to about 0.5 mL of a therapeutic agent, drug, or vaccine therein. The method may also include forming an access hole within each reservoir of the plurality of reservoirs. A cover layer may be bonded or thermally annealed to the flat panel wafer such that each of the cavities of the plurality of reservoirs are accessible only through each of the access holes. A plurality of reservoirs may be simultaneously filled with at least one of a therapeutic agent, drug, or vaccine. In certain embodiments, the method may include providing a bottom support layer adjacent the plurality of reservoirs. A device produced by this methodology is also intended herein.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

DESCRIPTION OF THE PREFERRED EMBODIMENTS

Figure 1:
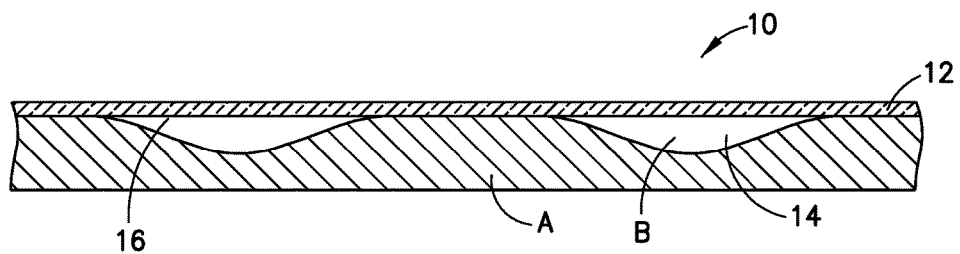
FIG. 1 is a front cross-sectional representation of a reservoir layer extending across a mold prior to a thermal slumping process in accordance with an embodiment of the present invented method.

The present invention is drawn to a method of manufacturing a miniaturized self-injection device, by producing a drug delivery component (the functional portion of the device containing elements necessary for performing the injection having a volume $V_{Funcational\_part}$), filling a reservoir of the functional part with a therapeutic agent such as a vaccine or drug, and placing the drug delivery portion in a housing device. According to one non-limiting embodiment, the manufacturing method incorporates manufacturing processes suitable for fabrication of integrated circuits, electronic packages, and other microelectronic or micro-electric-mechanical system (MEMS) devices. Other techniques used in the invented method of manufacture are adapted from the field of micromachining. However, the method of manufacture described below is intended only as a non-limiting exemplary method for manufacturing the miniaturized self-injection device. It is understood that the self-injection device of the present invention can be formed in numerous other ways which do not necessarily rely on semiconductor manufacturing principles and, nevertheless, fall within the scope of the invented method.

Self-injection devices manufactured using MEMS techniques may be miniaturized substantially compared with traditional drug delivery devices. Existing drug delivery devices, whether designed for intra-muscular, intradermal, or transdermal injections are designed based on functional considerations, specifically focusing on the elements of the device needed for drug delivery. The precise design of the "functional" elements is, thus, usually based on a set of techno-economic constraints associated with this primary function of drug delivery. This notion, which essentially focuses on a "minimalist design", can be efficiently described by a parameter, R, between 0 and 1, that we will call the "minimalism", and which we define as:

$$R = \frac{V_{Functional\_parts}}{V_{Total}}$$

In the equation, $V_{Total}$ is the total volume of the device, i.e., the volume of the entire (wholly assembled) device in conditions of immediate use by the user (i.e., removed from any associated packaging). $V_{Functional\_parts}$ is the volume of the functional part of the device. The "functional part" refers to the elements of the device necessary for fluid injection. In a typical injection syringe, "functional parts" include the delivery structure such as a needle, a reservoir for containing the liquid drug, and an expulsion mechanism such as a plunger. Thus, an essentially artistic object, such as a sculpture, has an R value of near 0, as it has relatively few functional parts.

It is noted that the volumes of the functional and non-functional parts of a drug delivery device can be calculated and compared in various ways. Most simply, the actual volume of the total device and the actual volume of the functional portion can be measured. Suitable methods for measuring these portions include fluid displacement where the device is placed in a fluid or gel and the displacement volume is measured. Alternatively, computer drafting (e.g., CAD) applications can accurately estimate the volumes of various shapes. In contrast, the R value could also be determined by comparing the actual volume of the device to the minimum volume that the device could be while still being capable of accomplishing its primary purpose. In essence, determining the volume $V_{Functional\_part}$ in this way requires imagining that the device is reduced in size as much as possible without losing functionality. In this case R is equal to the minimum possible volume divided by the actual volume. It is understood that interpreting R in this way captures the concept of minimalization of the present invention in the same way as the R equation described herein. However, the discrete values obtained using this second R equation are different than the values obtained using the earlier R equation. For clarity, the R values given in this specification are based on R calculated by measuring the actual volume of the functional part divided by the total volume.

For a conceptual "bare syringe" containing only a needle, barrel, and plunger, R=1. Syringes are also known which include additional structures such as outward extending flange portions to assist the user in gripping the syringe and pressing the plunger. However, these additional structural components are small when compared to the volume of the functional component of the syringe. Known syringes with gripping structures have an R value of about 0.95. Other syringe configurations are also known such as auto-injectors which have non-functional portions including a plastic housing which allows a user to more easily grip the device and protects the functional components of the syringe. An auto-injector also includes an activating button which, when pressed, triggers the plunger. Auto-injectors of this type have an R value of about 0.85. As is evident from the above-described devices, existing injection devices are characterized by an R parameter typically greater than 0.7. Such devices, while effective for drug delivery, are often difficult to use. These difficulties are greatly enhanced when individuals without medical training attempt to perform self-injections. By reducing the volume of the drug delivery portion of the self-injection device ($V_{Functional\_part}$), the R value of the self-injection device can be effectively reduced without increasing the total volume of the device ($V_{total}$) to an inconveniently large size.

Use of MEMS-type manufacturing techniques can also increase manufacturing capacity. Specifically, the manufacturing method reduces individual device cost by allowing for large scale batch manufacturing of the injection device with high throughput. Batch production is a manufacturing technique in which numerous articles are prepared in parallel rather than in an assembly line fashion in which only a single device is acted on at a time. It is envisioned that batch manufacturing will increase production rate for the injection device, thereby reducing the unit cost per device.

In one embodiment of the invented method, numerous drug delivery devices 10 are fabricated from a single flat panel wafer. The wafers are provided to a fabrication machine in a box or cartridge containing about 25 wafers. In one embodiment, each wafer is about 14 to 17 inches square and has a thickness of about 400 µm. The flat panel wafers may be composed of glass or other medical grade material suitable to be modified by thermal slumping. The flat panel wafer should be impermeable to water and/or oxygen to preserve the therapeutic agent and to increase the shelf life of the device. Further, the reservoir material should be generally inert and non-reactive with the therapeutic agent to prevent contamination from, for example, chemicals (e.g., leachables, polymerization promotors, unreacted monomer, etc.) which may diffuse from the substrate to the fluid agent.

The flat panel wafer can be produced by any acceptable method including float processing and fusion processing (also known as an overflow down draw process). The float process (also known as the Pilkington process) involves floating molten glass on a bed of molten metal to create a sheet of uniform thickness. In the fusion production method, molten glass is permitted to flow down opposite sides of a tapered trough forming two thin molten streams. The two glass streams rejoin or fuse at the base of the trough forming a single sheet having excellent uniformity of depth and composition. The fusion process is a technique for producing flat glass often used in the manufacture of flat panel displays. Advantageously, the technique produces glass with a more pristine surface, as the surface is not touched by molten metal. Glass produced by this technique is widely commercially available and is produced by companies including Corning, Samsung, and Nippon Electronic Glass. Alternatively, substrate materials including medical grade polymers and silicone could also be used within the scope of invented method.

Recent advances in glass fabrication techniques (especially in the field of flat glass for flat panel displays) have greatly increased the size of flat glass panels which are commercially available. In one embodiment of the present method, a square wafer layer of about 14 to 17 square inches which can be manufactured to contain 40 to 50 delivery devices is used as a substrate material. However, glass panels as large as 2×3 meters are presently commercially available. Using glass panels of several square meters or more to manufacture self-injection devices, according to the invented method, permits ultra-high throughput and allows for a significant reduction in unit cost per device.

With reference to FIG. 1, the flat panel is formed into a reservoir layer 12 having a plurality of reservoir cavities 14 according to a thermal slumping process. Initially, a bottom side 16 of the reservoir layer 12 is cleaned and dried. The reservoir layer 12 is then positioned over a refractory or slumping mold A, consisting of numerous depressions B of uniform diameter and depth, such that the bottom side 16 of the reservoir layer 12 contacts the top surface of the mold and extends over the depressions. Molds formed from numerous materials including, but not limiting to, aluminum, stainless steel, nickel, tungsten carbide, and silicon carbide, as well as ceramics, are known. Generally, the mold material should be able to maintain its form when exposed to temperatures in excess of 600° C. The mold should not deteriorate at high temperatures. It also should not stick to the substrate material when exposed to high temperatures. The mold material should also have good hardness and temperature stability. One ceramic material which can be used in a thermal slumping process, within the scope of the present invention, is MACOR ceramic manufactured by Ceramic Products, Inc. of Hasbrouck Heights, N.J.

In one embodiment, as shown in FIG. 1, the reservoir layer 12 and mold A are exposed to a temperature of 650° C. for about 11 hours thereby causing the reservoir layer 12 to deform so that portions of the layer 12 slump into the depressed areas B of the mold A thereby forming the fluidic reservoir cavities 14. After the mold A and reservoir layer 12 are cooled, the panel is released from the mold.

The reservoir cavity 14 can be any shape, which can be manufactured through thermal slumping with a large enough volume to hold the correct dose of a therapeutic agent. For example, the reservoir cavity 14 could be a hemisphere or a square. To promote the goal of overall miniaturization of the drug delivery device 10 of the self-injection device, the dimensions of the reservoir cavity 14 should be as small as possible, but sufficient to hold a single dose of the therapeutic agent. According to one embodiment of the invention, adopted for use with flu vaccine, the reservoir is 100 µL.

However, drug delivery devices made according to the invented method may be configured to include reservoirs having a volume of 0.5 mL or more.

Figure 2A:
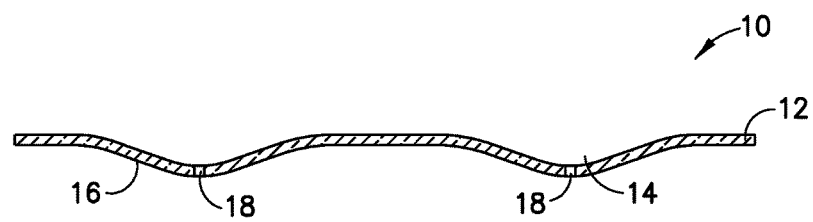
FIG. 2A is a front cross-sectional representation of the reservoir layer of FIG. 1 after the thermal slumping process in accordance with an embodiment of the present invented method.
Figure 2B:
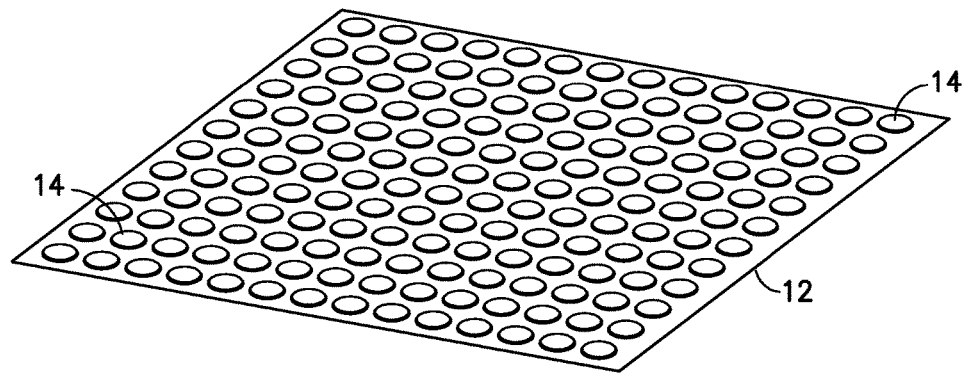
FIG. 2B is a perspective view of the reservoir layer of FIG. 1 having a plurality of reservoirs formed therein, in accordance with an embodiment of the present invented method.
Figure 2C:
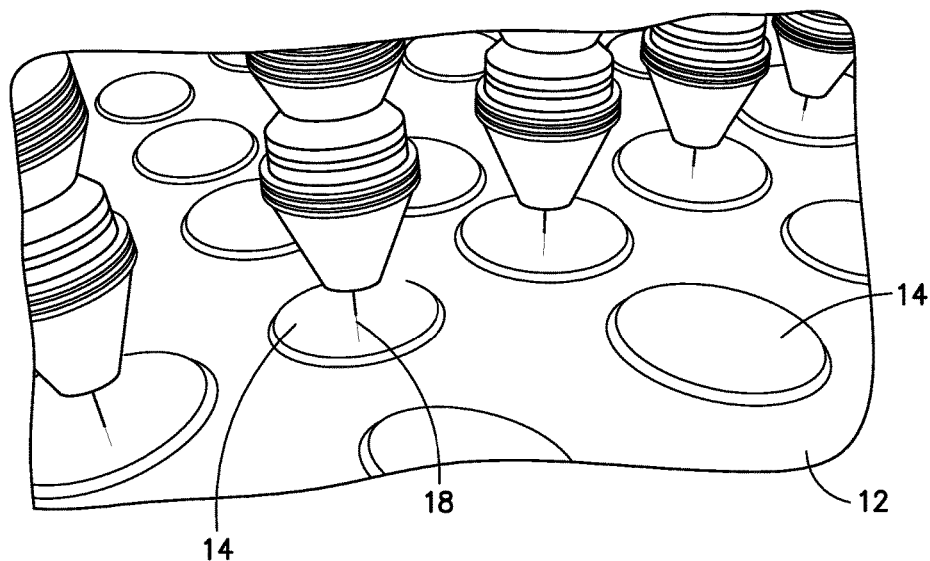
FIG. 2C is a schematic perspective representation of the process of creating holes in the reservoir layer of FIG. 1 to produce access holes in the plurality of reservoirs in accordance with an embodiment of the present invented method.

With reference to FIGS. 2A-2C, an access hole 18 is next formed in the reservoir cavity 14 to permit fluid access to and from the reservoir cavity 14. The access hole 18 may be formed by a drill or other apparatus capable of creating a hole in a glass substrate such as an awl or chisel. Drilling may be performed by a micromachining apparatus having a plurality of drill bits for drilling multiple holes at once. In one embodiment of the invention, the access hole 18 is adapted to receive a 30 gauge needle. Alternatively, the access hole 18 may be formed in the reservoir layer 12 before thermal slumping is performed. In either case, a reservoir layer 12 having a plurality of reservoir cavities 14 with access holes 18 is ultimately produced.

Figure 3A:
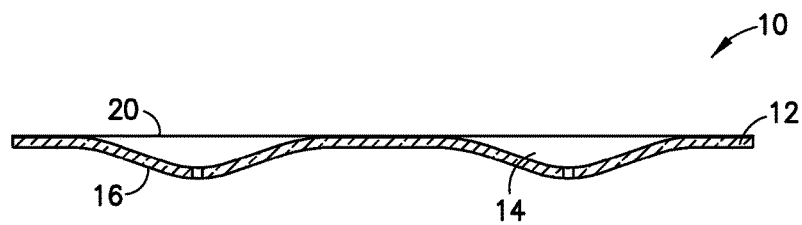
FIG. 3A is a front cross-sectional representation of the reservoir layer of FIG. 1 having a cover layer to form an enclosed reservoir in accordance with an embodiment of the present invented method.
Figure 3B:
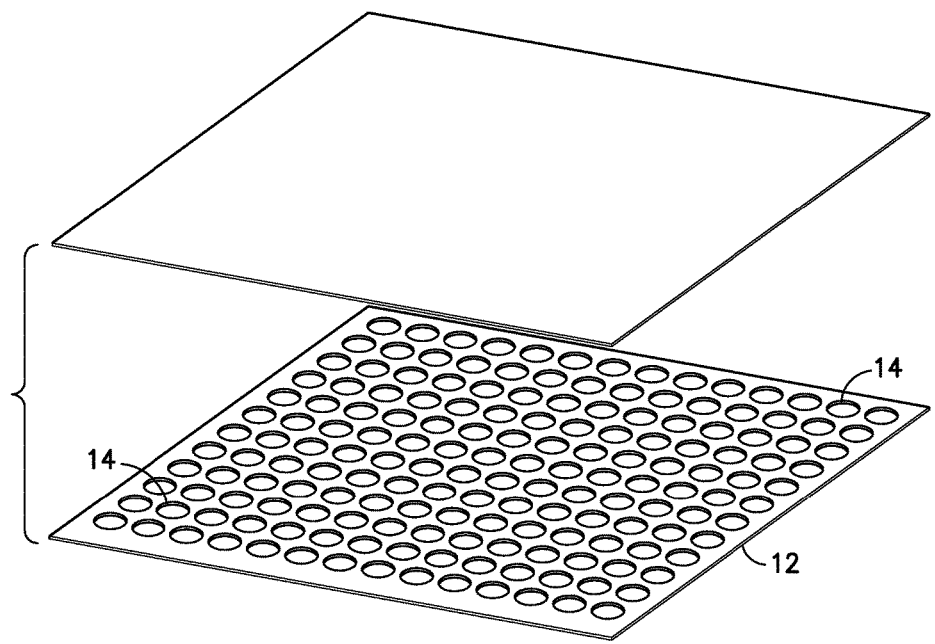
FIG. 3B is an exploded perspective view of the reservoir layer of FIG. 1 and the cover layer of FIG. 3A in accordance with an embodiment of the present invented method.
Figure 3C:
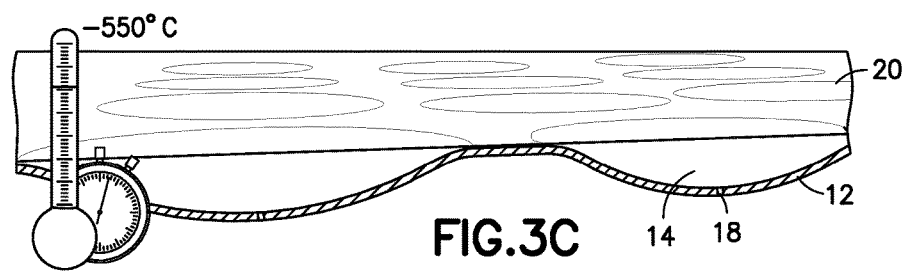
FIG. 3C is a perspective view of the reservoir layer of FIG. 1 and the cover layer of FIG. 3A during an annealing step in accordance with an embodiment of the present invention.
Figure 4:
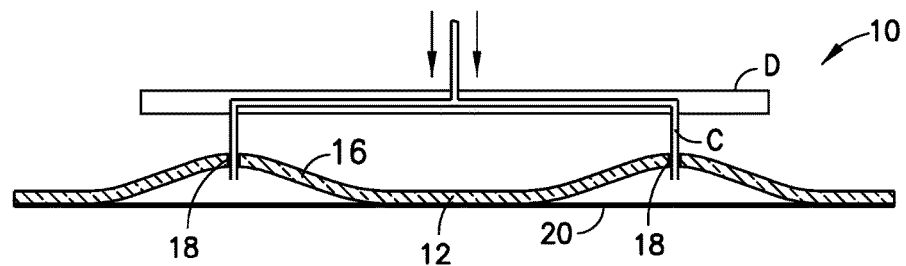
FIG. 4 is a cross-sectional front schematic representation of the reservoir of FIG. 3A in fluid connection with a counter wafer for filling in accordance with an embodiment of the present invented method.
Figure 5A:
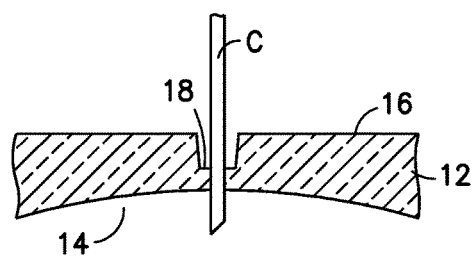
FIG. 5A is a cross-sectional schematic representation of filling of a drug delivery device in accordance with an embodiment of the present invention.
Figure 5B:
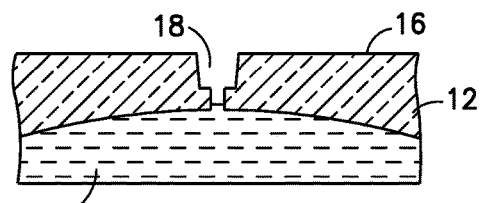
FIG. 5B is a cross-sectional front schematic representation of the filling of the drug delivery device of FIG. 5A in accordance with an embodiment of the present invention.
Figure 5C:
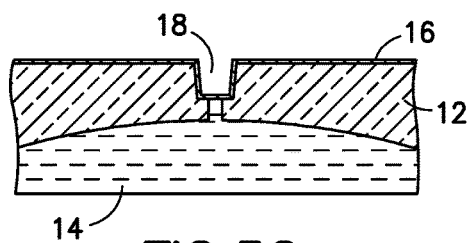
FIG. 5C is a cross-sectional front schematic representation of the filling of the drug delivery device of FIG. 5A in accordance with an embodiment of the present invention.

With reference to FIGS. 3A-3C, after the reservoir cavities 14 and access holes 18 are formed, the reservoir layer 12 is once again cleaned and dried. Afterwards, a cover layer 20 is provided. The cover layer 20 may be an ultra thin glass layer having a thickness of approximately 30 μm to 50 μm. The cover layer 20 is attached to the reservoir layer 12 through bonding and/or thermal annealing thereby enclosing the reservoir cavities 14 so that the cavities 14 are only accessible through access holes 18. In one non-limiting embodiment, the cover layer 20 is attached by thermal annealing where the glass layers are exposed to 550° C. for 11 hours to produce a bonded connection between the layers.

Figure 9A:
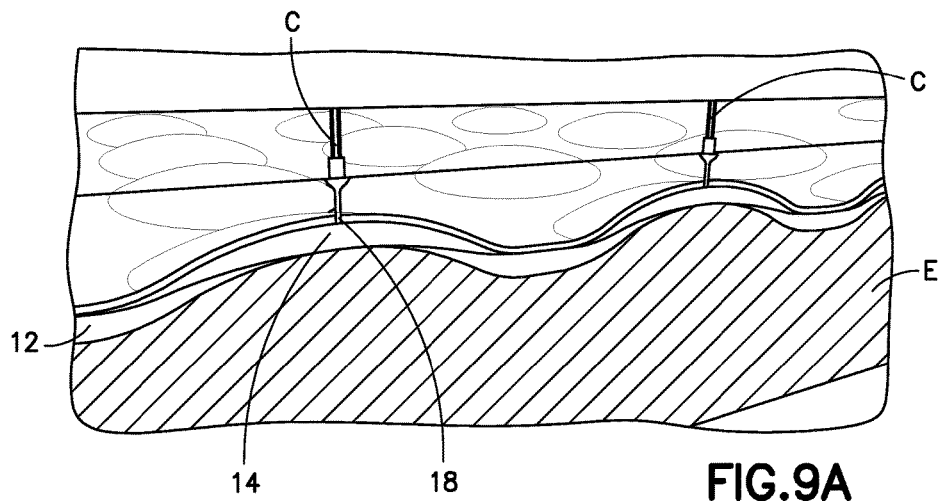
FIG. 9A. is a front schematic cross-sectional representation of the filling process for a reservoir of the drug delivery device of FIG. 7 with a rigid mold and a counter wafer.
Figure 9B:
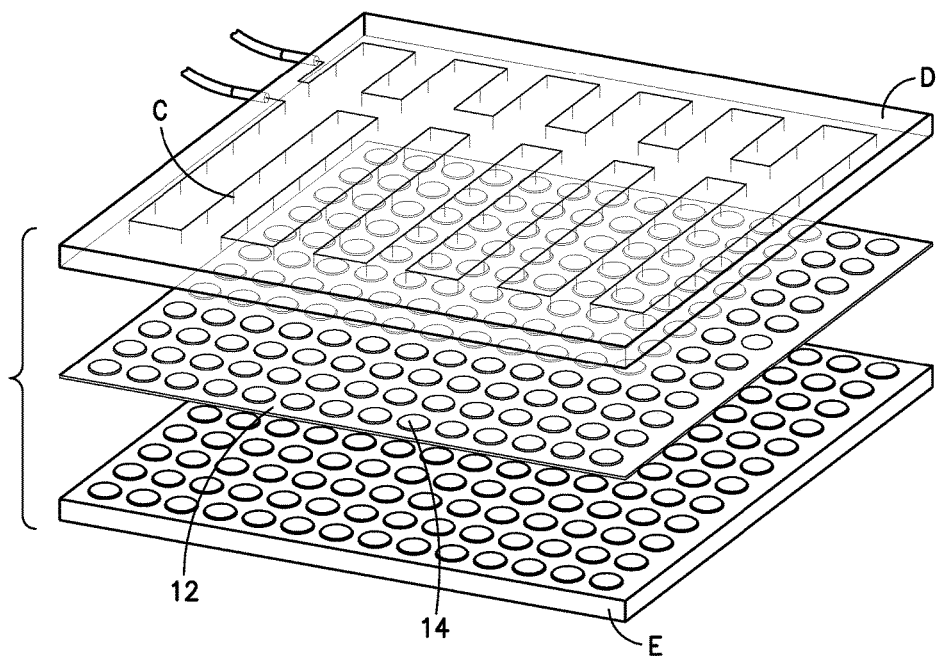
FIG. 9B is a front perspective schematic representation of the filling process for the drug delivery device of FIG. 7 with a rigid mold and counter wafer according to an embodiment of the present invented method.

With reference to FIGS. 9A-9B, the reservoir cavities 14 are next filled with a vaccine or drug to be delivered to the user. The reservoir cavities 14 may be filled by a counter wafer having a number of filling cannula C corresponding to the number of reservoir cavities 14 for injecting medicinal fluid into the reservoir cavities 14. In one non-limiting embodiment, the reservoir layer 12 is inverted and positioned in a rigid mold E. The mold E is used to force air from the reservoir 12 through the access hole 18 by pushing the reservoir layer 12 toward the cover layer 20. Once the air is removed, the cannula C of the counter wafer is inserted into the reservoir cavity 14 through the access hole 18. The mold is then removed so that the reservoir cavity 14 expands to its original shape. As the reservoir cavity 14 expands, medicinal fluid is drawn into the reservoir cavity 14 through the filling cannula C.

With reference to FIGS. 4 and 5A-5C, in an alternative embodiment, the reservoir cavities 14 are sealed through a vacuum suction method. According to the method, the reservoir layer 12 is inverted and a filling cannula C is inserted into the reservoir cavity 14 through the access hole 18. Air is pumped from the reservoir cavity 14 through the inserted cannula C to put the cavity under vacuum. With the cannula C still in place, fluid is then introduced to the cavity through the same filling cannula C. As a result of the fact that the reservoir cavity 14 is under vacuum, the exact volume of fluid required to fill the reservoir cavity 14 is extracted through the cannula C without external pumping of the fluid. In one non-limiting embodiment, filling is accomplished using a counter wafer D. The counter wafer D includes a fluid reservoir and a plurality of filling cannulae C that corresponds to each reservoir cavity 14 of the reservoir layer 12. The injection needles C of the counter wafer D are brought in contact with each individual reservoir cavity 14, so that each cavity 14 can be filled simultaneously.

After the filling cannula C is removed from the reservoir cavity 14, the reservoir layer 12 is covered with an ultra-thin polymer layer (not shown) to prevent the fluid from leaking from the reservoir cavity 14. The thin polymer layer is cured using a process such as UV curing. Optionally, the thin polymer layer is a hydrophobic polymer to repel the reservoir fluid from the opening. The polymer layer should also be easily breakable so that a small expulsion force is sufficient to break the layer to permit fluid flow during injection. The polymeric protective membrane optionally includes a UV-blocking composition. Reducing the UV exposure of the fluid prevents the fluid from breaking down or spoiling from prolonged UV exposure.

Figure 6:
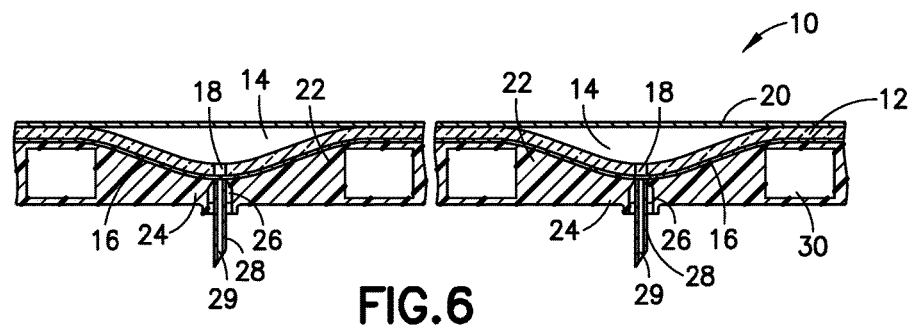
FIG. 6 is a front cross-sectional representation of a plurality of reservoirs and cover layers of FIG. 3A further connected to a bottom support layer in accordance with an embodiment of the present invention.
Figure 10:
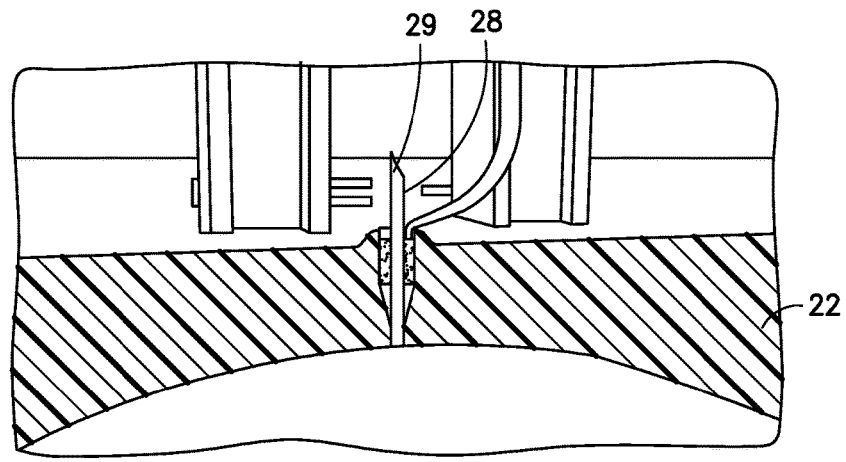
FIG. 10 is a front perspective schematic representation of a bottom structural support layer which receives a mini-needle from a "pick and place" machine.

With reference to FIGS. 6 and 10, a bottom structural support 22 is provided for attachment to the reservoir layer 12. The bottom structural support 22 may be formed from plastic. The bottom structural support 22 includes depressions 24 which correspond in shape and size to the reservoir cavities 14. Each depression 24 includes a needle socket 26. A mini-needle 28 is placed in the needle socket 26 using an automated "pick and place" machine. The mini-needle 28 is anchored to the bottom layer by a glue or adhesive and may be set using an ultra-violet curing technique. The mini-needle 28 is a hollow needle formed from metal or other suitably strong material. "Pick and Place" machines were developed for use in the electronics industry and are similar to machines used for placing transistors on a circuit board. The machines are highly modular and can be configured to insert the mini-needles with the desired positioning accuracy. In addition, such machines are capable of exceptionally high throughput; a typical machine can be configured to place in excess of 20,000 needles per hour. An exemplary "pick and place" machine is the TAL 9000 manufactured by Muehlbauer AG Tech International of Roding, Germany.

The mini-needle 28 may further include a stopper material (not shown) to prevent the fluid from being expelled from the reservoir prematurely. For example, a thin breakable film or membrane may be included within the needle channel. The film or membrane should be sufficiently strong and stable to prevent the fluid from escaping from the reservoir. However, once the injection device is activated, and an expulsion mechanism begins to reduce the volume of the reservoir cavity, the force applied to the thin membrane is increased. In response to this increase in force, the film or membrane breaks allowing fluid to pass through the needle for delivery to the user. A needle is attached to the needle socket using a pick and place machine. The needle is attached to the structural needle socket using an adhesive.

Alternatively, the bottom structural support 22 having the needle socket 26 may first be affixed to the reservoir layer 12. After the support 22 is affixed, the mini-needle 28 may then be attached to the needle socket 26 thereby establishing fluid communication between the reservoir cavity 14 and a tip 29 of the mini-needle 28 through the access hole 18 of the reservoir layer 12.

The bottom structural support 22 may further include actuation functionality. The actuation functionality may be a mechanical element such as a mechanical button 30 which actuates the mechanical process of expelling medicinal fluid contained in the reservoir cavity 14. Alternatively, the actuation functionality may be an on/off type switch which actuates an electronic apparatus such as a heating coil to actuate the expulsion mechanism.

Figure 11:
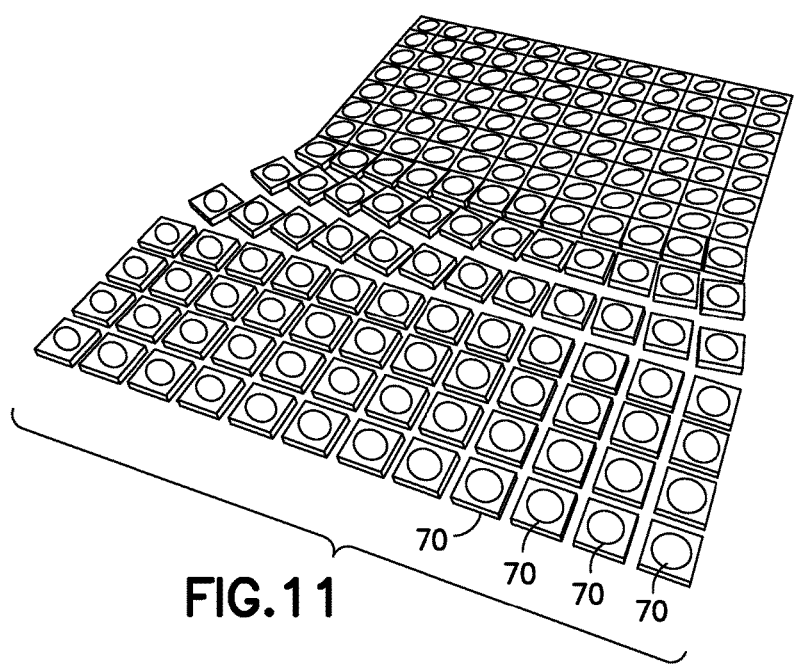
FIG. 11 is a perspective schematic representation of the dividing step in which the drug delivery devices of FIG. 7 are separated from one another according to an embodiment of the present invented method.

With reference to FIG. 11, once the layers, namely the bottom support layer 22, reservoir layer 12, and cover layer 20, for each reservoir cavity 14 are assembled, the composed layers are divided into individual injection devices. The composed layers may be divided by any suitable process capable of making exact and small diameter cuts in the composed layers rapidly. One cutting process well suited for this application is laser cutting. Mechanical and plasma cutting techniques can also be adapted for dividing the larger wafer into individual injection devices. In one embodiment, individual injection devices 70 (i.e., MEMS chips), as shown in FIG. 11, have dimensions of 30×30×2 mm. In another embodiment, the individual injection devices 70 have dimensions of 1.5×1.5×3 mm.

Other elements of the actuation and an expulsion mechanism may be included in upper functional layers 32 which are affixed to a top surface of cover layer 20. For example, with reference to FIG. 7, the actuation and expulsion mechanism consisting of an activation reservoir 34 containing water and an expulsion reservoir 36 containing hydrophilic beads 38. The actuation reservoir 34 may be contained in an actuation layer 35. The expulsion reservoir 36 may be included in an expulsion layer 37. The hydrophilic beads 38 expand when contacted with water. As the beads 38 expand, the beads 38 force the cover layer 20 toward reservoir cavity 14 to expel fluid contained within the cavity 14. In use, when the device is activated, the water contained in the activation reservoir 34 is permitted to flow to the expulsion reservoir 36 to begin the process of expelling fluid from the reservoir cavity 14. The upper functional layers 32 may further include a pressure vessel layer 40 located between the cover layer 20 and the actuation layer 35. The pressure vessel layer 40 includes an empty space 42 to relieve pressure on the reservoir cavity 14 exerted by the expanding expulsion reservoir 36. As a result of a pressure vessel layer 40, air contained in space 42, rather than the actuation layer 35 itself, exerts force on the cover layer 20 to force fluid contained within reservoir cavity 14 from the device. All of the upper functional layers 32 may be formed by a lamination process, in which the layers 32 are sequentially deposited on and adhered to the previous layer.

Figure 7:
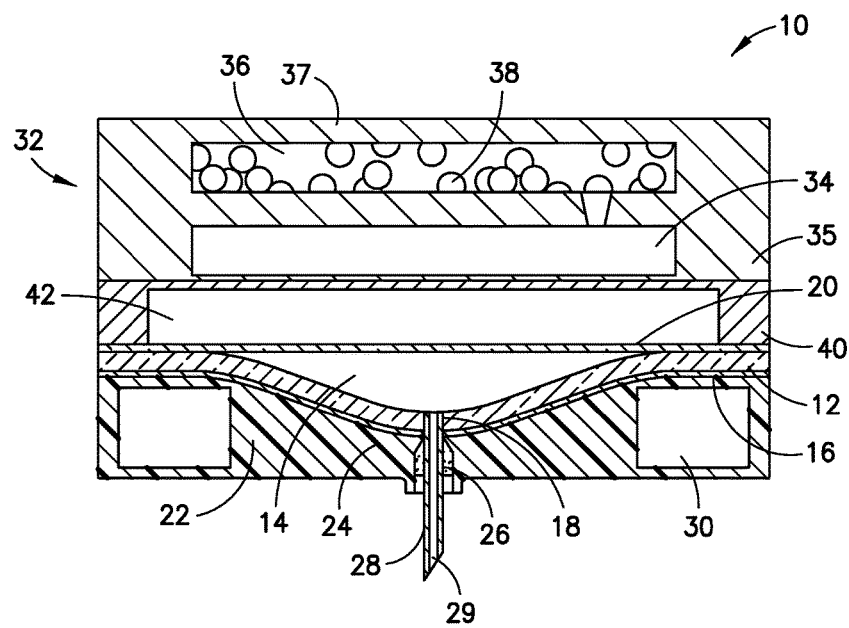
FIG. 7 is a front cross-sectional representation of a drug delivery portion of the self-injection device formed in accordance with an embodiment of the present invention.

It is noted, that the expulsion 36 and activation reservoirs 34 depicted in FIG. 7 are one example of a drug delivery device which can be manufactured within the scope of the present invention. It is understood that different expulsion mechanisms, including but not limited to, thermal expanding layers, flowable material such as paraffin wax, micropumping mechanical devices, and others can be configured to work with the device manufactured by the invented method. Similarly, activation mechanisms, including but not limited to, buttons, electronic switches, and temperature sensors may also be used within the scope of the invented method.

The beads 38 and other actuation elements and mechanical structures are placed using similar micromanufacturing techniques to the method for placing the mini-needle within the reservoir cavity 14 described above. As described above, it is desirable to place components according to a batch protection method in which components for multiple injection devices are placed simultaneously.

Figure 8A:
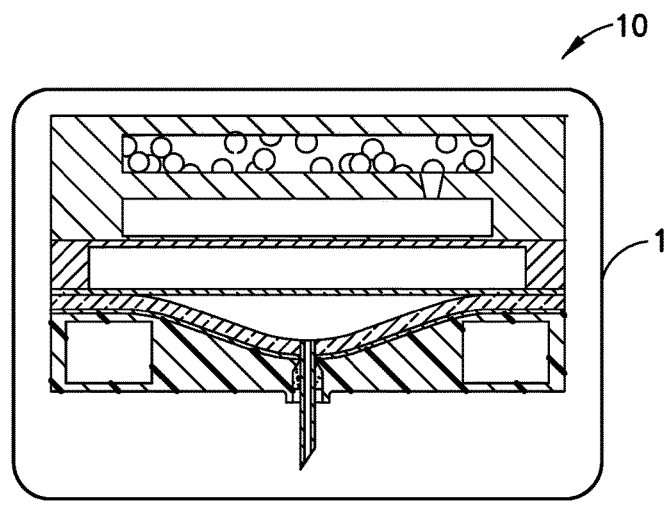
FIG. 8A is a front cross-sectional representation of the drug delivery portion of FIG. 7 enclosed within a housing according to an embodiment of the present invented method.
Figure 8B:
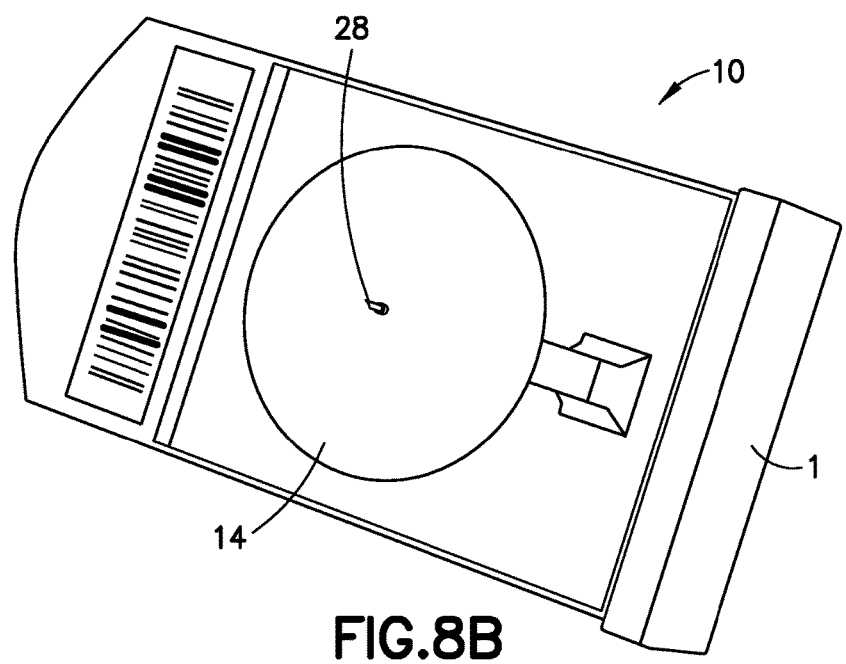
FIG. 8B is a perspective view of the drug delivery portion of FIG. 7 enclosed within a housing according to an embodiment of the present invented method.

With reference now to FIGS. 8A and 8B, once the drug delivery device 10 of the self-injection device is fully assembled, filled, and divided, the drug delivery device 10 of the device is placed in a housing 1. The housing 1 can be made from any structurally sound and visually appealing material such as high density polymers, brushed aluminum, or other metallic alloys. The housing 1 may contain additional elements such as electronics, power supply, physical sensors, or a wireless (e.g., Bluetooth) antenna. The housing 1 may further include elements completely unrelated to self-injection such as a watch and watch face, thermometer, or non-functional ornamentation. The housing 1 may also include packaging or protective material such as foam to protect the drug delivery device 10 of the device and any supplementary electronic components. The housing 1 may also simply enclose empty space. In any case, the housing volume is greater than necessary merely to contain the drug delivery device 10.

The drug delivery device 10 may be held in place within the housing by any affixation means commonly employed in the electronics industry for such purposes. For example, the drug delivery device 10 could be screwed or stapled in place using small affixing members. The delivery device 10 may also be secured by an adhesive. In one embodiment, the injection device may be placed in the housing using a "pick and place" style machine.

As stated above, a single injection device 70 can be configured to hold up to about 0.5 mL of liquid. Drug delivery devices for delivering a dose greater than about 0.5 mL can be constructed by stacking a plurality of MEMS chips, each containing an individual reservoir. In this way, a device can be constructed for delivering 1 mL or more of a therapeutic agent to a patient. Further, even with self-injection devices with larger reservoir volumes manufactured by the invented method, the total functional volume is still smaller than a syringe having the same reservoir volume because in the MEMS type device, the actuation mechanism is embedded on the chip itself. In contrast, when a syringe is filled, the plunger extends beyond the reservoir, meaning the functional volume of the syringe is at least twice the volume of the reservoir.

When considering the method of manufacture for the self injection device, it is understood that multiple steps which require microfrabrication (e.g., "pick and place") machines could be performed together. For example, the steps of dividing the devices by cutting the wafer and placing the individual wafers in housings could be performed simultaneously by the same "pick and place" type machine. Additionally, the same machine could be used to simultaneously fill the reservoirs and place the mini-needles within the reservoir.

Additional manufacturing concerns for the injection devices arise from the fact that these devices are being used for medical purposes and, accordingly, must follow FDA protocols for the manufacture of medical devices.

What is claimed is:

1. A method of making a delivery device for a therapeutic agent, drug, or vaccine, comprising:
   providing a flat panel wafer;
   forming a plurality of reservoirs, with each reservoir defining a cavity, within the flat panel wafer;
   attaching a cover layer across the plurality of reservoirs;
   filling the plurality of reservoirs with at least one of the therapeutic agent, drug, and vaccine to form a plurality of filled reservoirs;
   providing a housing portion adjacent each of the plurality of filled reservoirs to form a composed layer; and
   separating the composed layer into a plurality of delivery devices, wherein each delivery device comprises a reservoir.

2. The method of claim 1, wherein the flat panel wafer comprises at least one of glass and silicon.

3. The method of claim 1, wherein the forming a plurality of reservoirs within the flat panel wafer is achieved by thermal slumping.

4. The method of claim 1, wherein the flat panel wafer has a thickness of about 400 µm.

5. The method of claim 1, wherein the flat panel wafer is substantially impermeable to water and oxygen, and wherein the flat panel wafer is formed of a material that is substantially inert or coated with a material that is substantially inert.

6. The method of claim 1, wherein the flat panel wafer is formed by at least one of float processing and fusion processing.

7. The method of claim 1, wherein the flat panel wafer has an initial dimension of from about 14 square inches to about 17 square inches, and wherein from about 40 to about 50 delivery devices are produced from the flat panel wafer.

8. The method of claim 1, further comprising forming an access hole within each reservoir of the plurality of reservoirs.

9. The method of claim 8, wherein the cover layer is bonded or thermally annealed to the flat panel wafer such that each of the cavities of the plurality of reservoirs are accessible only through the access holes.

10. The method of claim 1, further comprising sealing the filled reservoirs with a thin polymer layer.

11. The method of claim 1, wherein the housing portion comprises a bottom support layer.

12. The method of claim 1, wherein the step of filling the plurality of reservoirs comprises:

introducing a filling cannula to the reservoir;

removing air contained in the reservoir from the reservoir, through the filling cannula, to create a vacuum in the reservoir;

passively drawing the therapeutic agent, drug, or vaccine into the reservoir through the filling cannula, as a result of a pressure difference between the vacuum in the reservoir and the therapeutic agent, drug, or vaccine;

removing the filling cannula from the reservoir; and covering a hole formed by the filling cannula with an adhesive film to seal the reservoir.

13. The method of claim 12, wherein a plurality of the filling cannulae are disposed on a counter-wafer, and wherein the counter-wafer is configured such that each filling cannula is simultaneously introduced to a reservoir for simultaneously filling the plurality of reservoirs.

14. The method of claim 1, further comprising providing a plurality of needles, each needle engageable with a single filled reservoir of the plurality of reservoirs.

* * * * *